United States Patent [19]

Schachar

[11] Patent Number: 4,606,623
[45] Date of Patent: Aug. 19, 1986

[54] METHOD FOR MEASURING INTRAOPERATIVE AND IMMEDIATE POSTOPERATIVE EFFECTS OF RADIAL KERATOTOMY

[76] Inventor: Ronald A. Schachar, 1020 Highway 75 North, Denison, Tex. 75020

[21] Appl. No.: 316,665

[22] Filed: Oct. 30, 1981

[51] Int. Cl.$^4$ .............................................. A61B 3/10
[52] U.S. Cl. .................................................. 351/212
[58] Field of Search ................................ 351/211, 212

[56] References Cited

U.S. PATENT DOCUMENTS

| | | | |
|---|---|---|---|
| 3,895,860 | 7/1975 | Townsley | 351/212 |
| 4,019,813 | 4/1977 | Cornsweet et al. | 351/212 |
| 4,157,859 | 6/1979 | Terry | 351/212 |

Primary Examiner—John K. Corbin
Assistant Examiner—P. M. Dzierzynski
Attorney, Agent, or Firm—Jerry W. Mills; Gregory M. Howison

[57] ABSTRACT

A method and apparatus for measuring the intraoperative and immediate postoperative effects of radial keratotomy are provided. Essentially, the method includes the steps of measuring the preoperative corneal thickness and radial distance along multiple meridians, plotting the preoperative internal radius of curvature of the cornea, measuring the intraoperative or immediate postoperative radial distances along multiple meridians, plotting the intraoperative or immediate postoperative internal radius of curvature and predicting the resulting anterior radius of curvature of the cornea. The apparatus of the present invention includes apparatus for illuminating the cornea, forming profile images of the cornea, measuring the radial distance and thickness along multiple meridians, plotting the preoperative and intraoperative or immediate postoperative internal radii of curvature, determining the resulting anterior radius of curvature of the cornea in any and all meridians and displaying the calculated and measured data.

9 Claims, 4 Drawing Figures

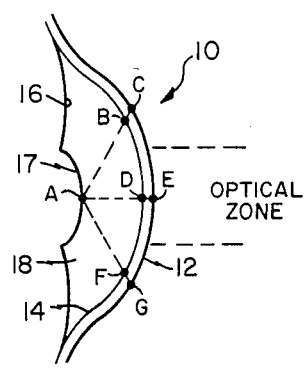
FIG. 1
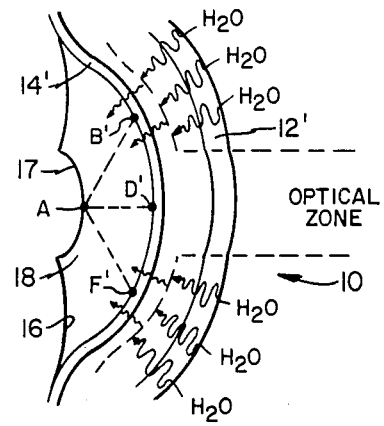
FIG. 2
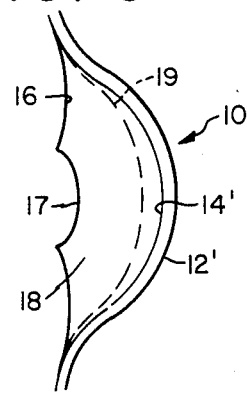
FIG. 3
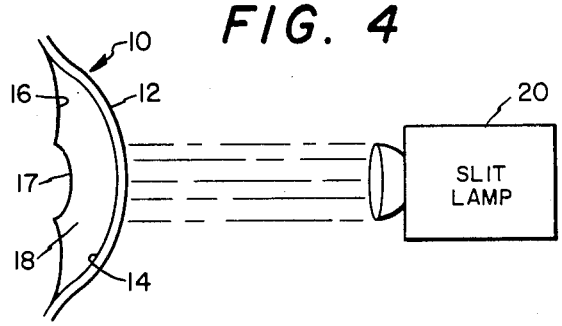
FIG. 4
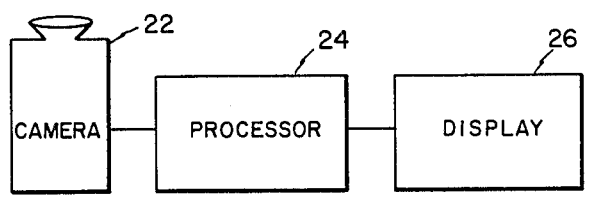

METHOD FOR MEASURING INTRAOPERATIVE AND IMMEDIATE POSTOPERATIVE EFFECTS OF RADIAL KERATOTOMY

TECHNICAL FIELD

This invention relates to a method for measuring the intraoperative and immediate postoperative effects of radial keratotomy. More specifically, the invention relates to a method for measuring the intraoperative or immediate postoperative change in the internal radius of curvature of the cornea, and then predicting the resulting anterior radius of curvature of the cornea.

BACKGROUND ART

Radial keratotomy is a surgical method that consists of forming incisions of a desired depth and location on the surface of the cornea to change the curvature of the cornea. This operation is used to correct myopia and other defects which relate to the curvature of the cornea. Although it has been suggested that radial keratotomy works by peripheral bulging of the cornea, the more accepted view is that the effect is due to the entire cornea stretching. After radial keratotomy, the cornea is weakened by the incisions therein and the intraocular pressure stretches the cornea, with most of the stretching occurring near the optical zone. The stretching increases the radius of curvature of the cornea, thereby flattening the cornea and improving the vision of the patient. The deeper the incisions made during the operation and the smaller the optical zone the more the cornea will stretch. Deepening the incisions near the limbus will increase the effect, but deepening the incisions near the optical zone will have a greater effect. The maximum effect is achieved if the incisions are at maximal depth. It is thus important to carefully monitor the incisions and the resulting changes in the cornea to insure a successful operation.

A keratometer is currently used to determine the radius of curvature of the cornea and thereby calculate the optical power of the cornea. During the performance of radial keratotomy, however, the corneal stroma swells because of corneal edema which is caused by the incisions through the epithelium. This edema is only temporary and will dissipate as the cornea heals (approximately 2-6 months). As a result, any measurement of the radius of curvature of the anterior surface of the cornea during the operation or in the immediate postoperative period will not be correct in predicting the final outcome of the surgery. Thus, one must wait months before the full effects of radial keratotomy can be measured using currently available methods. A need exists, therefore, for a method and apparatus for measuring the intraoperative and immediate postoperative effects of radial keratotomy to enable one to immediately predict the effects (i.e., the change in the radius of curvature of the anterior surface of the cornea) of the surgery.

DISCLOSURE OF THE INVENTION

In accordance with the present invention, a method and apparatus for measuring the intraoperative and immediate postoperative effects of radial keratotomy are provided. Essentially, the method comprises measuring the change in the internal radius of curvature of the cornea. The internal radius of curvature can be accurately measured intraoperatively and in the immediate postoperative period because only the anterior surface of the cornea is significantly affected by edema. Because the thickness of the cornea (approximately 0.5 mm to 0.7 mm) is approximately the same before and several months after radial keratotomy, the resulting anterior radius of curvature of the cornea can be predicted if one can determine the change in the internal radius of curvature.

To measure the change in the internal radius of curvature of the cornea and thereby predict the postoperative anterior radius of curvature of the cornea, the internal radius of curvature and thickness of the cornea are first measured preoperatively. This is done along multiple meridians. The radial keratotomy is then performed and the resulting internal radius of curvature of the cornea is similarly measured. As noted above, since the cornea returns to its original preoperative thickness once it is fully healed, the final postoperative anterior radius of the cornea can be predicted from the preoperative corneal thickness and change in the internal radius of curvature.

In accordance with the preferred embodiment of the present invention, a preoperative profile image of the cornea is prepared and the thickness of the cornea is measured along multiple meridians and the more meridians used to prepare the profile image, the more accurate the image will be. This information is then used to plot a preoperative profile image of the cornea in any and all meridians. Following the radial keratotomy, another profile image of the cornea is similarly prepared except that the corneal thickness is not measured. Using the change in the internal radius of curvature shown by the profile images and the preoperative corneal thickness, the resulting anterior radius of curvature of the cornea can be immediately and accurately predicted in any and all meridians. The resulting dioptric power of the cornea may also be calculated.

BRIEF DESCRIPTION OF THE DRAWINGS

FIG. 1 is a profile image of the cornea in preoperative period.

FIG. 2 is a profile image of the cornea in the intraoperative or immediate postoperative period demonstrating corneal edema.

FIG. 3 is a profile image of the cornea in the postoperative period after the cornea has fully healed.

FIG. 4 is a schematic illustration of a preferred embodiment of the present invention.

DETAILED DESCRIPTION OF THE PREFERRED EMBODIMENT

In accordance with the present invention, a method and apparatus for measuring intraoperative and immediate postoperative effects of radial keratotomy are provided. The method comprises measuring the preoperative corneal thickness and the change in the internal radius of curvature of the cornea after radial keratotomy and predicting the resulting anterior radius of curvature of the cornea.

Referring now to FIG. 1, a preoperative profile image of the cornea 10 is illustrated. The anterior 12 and internal 14 surfaces of the cornea are shown as well as the iris 16, lens 17 and anterior chamber 18. In accordance with the present invention the cornea 10 is illuminated and photographed. The corneal thickness and radial distances of the internal 14 corneal surface are then measured along multiple meridians. As shown in FIG. 1, the radial lines AB, AD and AF represent the radial distances from the internal corneal surface 14 and the radial lines BC, DE and FG represent the corneal thickness along each meridian. Using these corneal thicknesses and radial distances a plot of the preoperative corneal thickness and internal radius of curvature is prepared.

FIG. 2 is a profile image of the cornea 10 in the intraoperative or immediate postoperative period demonstrating edema around the incisions, with less edema occurring in the optical zone thereby producing the relative peripheral bulging of the cornea 10. When the cornea 10 is incised it is weakened and the intraocular pressure stretches the entire cornea 10. Both the anterior 12' and internal 14' surfaces of the cornea 10 are stretched, but only the anterior surface 12' is predominantly affected by corneal edema.

Keratometers, the most common of which are made by Bausch & Lomb, American Optical, Keller, Haag Strait and Terry Operating Keratometer, project an object of a known size onto the cornea and the size of the reflected image is then measured to determine the magnification (actually minification, since the cornea is convex). As a result of the edema, however, the corneal stroma and epithelium are swollen and an accurate measurement of the anterior radius of curvature of the cornea 10 cannot be obtained using a keratometer or other devices. Because the internal surface 14' of the cornea 10 is not substantially affected by corneal edema, the internal radius of curvature of the cornea 10 can be accurately measured intraoperatively or in the immediate postoperative period. In accordance with the present invention, the radial distance of the internal surface of the cornea 14' is measured along multiple meridians intraoperatively or in the immediate postoperative period. As shown in FIG. 2, the radial distances are represented by the lines AB', AD' and AF'. Using these radial distances a plot of the intraoperative or immediate postoperative internal radius of curvature is prepared. Then, using the preoperative corneal thickness along each meridian, a plot of the resulting anterior radius of curvature of the cornea can be immediately and accurately prepared and the effect of the surgery determined.

FIG. 3 is a profile representation of the cornea 10 in the postoperative period after the cornea 10 has healed and the bulging has subsided. The dotted line 19 represents the preoperative radius of curvature.

The profile images of the cornea can be obtained, for example, by illuminating the cornea with a light source and then photographing the cornea. Any suitable light source will suffice, but a slit lamp is preferred. To avoid the necessity for developing film, it is preferred that a video camera be used. Further, it is preferred that the plots of the profile images of the cornea be prepared by a processor capable of digitizing the video images of the cornea. The processor should also be capable of predicting the resulting anterior radius of curvature from the measured preoperative corneal thickness and change in the internal radius of curvature. In the preferred embodiment, the foregoing data is displayed on a display board for viewing during the surgery.

Referring now to FIG. 4, a schematic illustration of the system for performing the method of the present invention in its preferred embodiment is shown. A light source 20 or other illuminating apparatus is positioned so that the light therefrom illuminates the cornea 10. As noted earlier, light source 20 is preferably a slit lamp. While the cornea 10 is illuminated, a camera 22 observes a profile image of the cornea 10. Again, any camera or video apparatus for photographing or forming a profile image of the cornea will suffice, but to avoid the need for developing film and save time, a video camera 22 is preferred. The image is then fed to a suitable apparatus for digitizing the profile image, i.e., a digitizing processor 24. Processor 24 should be capable of forming the profile images of the cornea, measuring the preoperative corneal thickness and radial distances of the internal corneal surface along multiple meridians (as shown in FIG. 1), measuring the intraoperative or immediate postoperative radial distances of the internal corneal surface along the same preoperative meridians (as shown in FIG. 2) and predicting the resulting anterior radius of curvature of the cornea after it has completely healed. The resulting dioptric power of the healed cornea may also be calculated. These measurements and calculations assist in controlling both the spherical myopic correction and the astigmatic correction. It is understood that in all measurements the processor will take into account the index of refraction of the cornea and any changes in the index of refraction which occur as a result of hydration.

The processor 24 is preferably connected to a display board 26 which displays the radii of curvature and thickness of the cornea for quick observation. The display board 26 could also comprise a microscope with the display in the microscopic field thereof such that a surgeon performing radial keratotomy could view the information through the oculars during surgery.

Whereas the invention has been described with respect to preferred embodiments, it is apparent to one skilled in the art that various modifications will now be apparent and such are intended to be within the scope of the appended claims.

What is claimed is:

1. A method for measuring intraoperative and immediate postoperative effects of astigmatic correctional surgery and radial keratotomy, comprising:
    measuring the preoperative thickness of the cornea;
    measuring the preoperative radius of curvature of the posterior surface of the cornea;
    measuring the radius of curvature of the posterior surface of the cornea when edema is present as a result of surgery, the radius of curvature of the posterior surface of the cornea not substantially altered by edema; and
    determining the anterior radius of curvature of the cornea that will result after the cornea has healed and returned to the preoperative thickness.

2. The method as recited in claim 1 wherein the preoperative corneal thickness and the preoperative and intraoperative or immediate postoperative internal radii of curvature of the cornea are determined by:
    measuring the actual corneal thickness and radial distances of the internal corneal surface of the cornea along multiple meridians in the preoperative period;
    measuring the actual radial distance of the internal corneal surface along multiple meridians in the intraoperative or immediate postoperative period; and
    preparing profile images of the cornea from the measured corneal thickness and radial distances.

3. The method as recited in claim 2 wherein the actual preoperative thickness and actual preoperative and intraoperative or immediate postoperative radial distances are determined by:

illuminating the cornea of the eye with a light source;
forming a profile image of the illuminated cornea; and
measuring the preoperative thickness and radial distances of the cornea along multiple meridians and measuring the intraoperative or immediate postoperative radial distance of the cornea along multiple meridians.

4. The method as recited in claim 3 wherein the light source is a slit lamp.

5. The method as recited in claim 3 wherein a video camera is used to form the profile image of the illuminated cornea.

6. The method as recited in claim 3 or 5 wherein the profile image of the cornea is fed into a processor which digitizes the image, measures the radial distances and thickness of the cornea, plots the radii of curvature of the cornea and determines the resulting anterior radius of curvature of the cornea.

7. The method as recited in claim 3 further comprising feeding the measured internal radii of curvature, thickness and resulting anterior radius of curvature of the cornea to display means for viewing.

8. The method as recited in claim 7 wherein the display means are located within a microscopic field of a microscope having oculars such that the internal radii of curvature, thickness and resulting anterior radius of curvature can be viewed by looking through the oculars of the microscope while performing the surgery.

9. The method as recited in claim 6 wherein the radial distances and thickness are measured photographically.

* * * * *